United States Patent
Robertson et al.

(10) Patent No.: US 6,679,257 B1
(45) Date of Patent: Jan. 20, 2004

(54) BREATHING ASSISTANCE APPARATUS

(75) Inventors: Christopher John Robertson, Dunedin (NZ); Nicholas Charles Alan Smith, Auckland (NZ); Lewis George Gradon, Auckland (NZ)

(73) Assignee: Fisher & Paykel Limited, Auckland (NZ)

( * ) Notice: Subject to any disclaimer, the term of this patent is extended or adjusted under 35 U.S.C. 154(b) by 0 days.

(21) Appl. No.: 09/629,536

(22) Filed: Jul. 31, 2000

Related U.S. Application Data

(63) Continuation-in-part of application No. 09/326,478, filed on Jun. 4, 1998, now abandoned.

(30) Foreign Application Priority Data

| Aug. 13, 1998 | (NZ) | ................................. 331355 |
| Aug. 10, 1999 | (NZ) | ............................. 43458/99 |
| Sep. 29, 1999 | (NZ) | ................................. 500000 |

(51) Int. Cl.[7] ............................................ A61M 16/00
(52) U.S. Cl. ............................ 128/204.18; 128/201.26
(58) Field of Search ................ 128/200.24, 200.28, 128/201.26, 202.28, 204.18, 204.21, 204.23, 204.26, 203.12, 207.14, 205.29, 201.22, 201.27, 201.11, 200.29, 859–862, 206.21, 206.29; 405/186, 187; 602/902; D24/110.5, 164

(56) References Cited

U.S. PATENT DOCUMENTS

| 1,177,383 A | | 3/1916 | Claren | |
| 1,592,345 A | | 7/1926 | Drager | |
| 3,013,554 A | * | 12/1961 | Safar et al. | ............ 128/202.28 |
| 3,060,927 A | * | 10/1962 | Gattone | .................. 128/202.28 |
| 3,079,916 A | * | 3/1963 | Marsden | ................. 128/202.28 |
| 3,139,088 A | * | 6/1964 | Galleher | ................. 128/206.29 |
| 3,303,845 A | * | 2/1967 | Detmer | .................. 128/202.28 |
| 3,670,726 A | | 6/1972 | Mahon et al. | |

(List continued on next page.)

FOREIGN PATENT DOCUMENTS

| AU | 19 9943458 | 3/2000 |
| AU | 20 0048919 | 10/2000 |
| DE | 3 543931 A1 | 6/1987 |
| DE | 4 445652 A1 | 6/1996 |
| EP | 0 818213 A2 | 1/1998 |
| EP | 0 845277 A2 | 6/1998 |
| EP | 0979662 | 2/2000 |
| EP | 1075848 | 2/2001 |
| JP | 20 00051357 | 2/2000 |
| JP | 20 01079091 | 3/2001 |

(List continued on next page.)

OTHER PUBLICATIONS

SDDS Report, A Quarterly Publication of the Sleep Disorders Dental Society, Oral Positive Airway Pressure by the OPAP Dental Appliance Reduces Mild to Severe Obstructive Sleep Apnea, Jun. 1998, p. 1 and 4.

(List continued on next page.)

Primary Examiner—Weilun Lo
Assistant Examiner—Teena Mitchell
(74) Attorney, Agent, or Firm—Trexler, Bushnell, Giangiorgi, Blackstone & Marr, Ltd.

(57) ABSTRACT

A mouthpiece for oral delivery for oral delivery of CPAP treatment has a vestibular shield for location between the teeth and lips/cheeks of a wearer. The vestibular shield is formed from a very supple material and is dimensioned to extend laterally into the buccal vestibule and vertically to overlap the gums. A gases pathway is provided through the vestibular shield and may include a hard plastic insert through the shield. A connection for connecting the mouthpiece to a breathing circuit is provided which reduces the transfer of forces caused by movement therebetween.

37 Claims, 6 Drawing Sheets

U.S. PATENT DOCUMENTS

| | | | |
|---|---|---|---|
| 3,682,164 A | * | 8/1972 | Miller ..................... 128/136 |
| 3,963,856 A | | 6/1976 | Carlson et al. |
| 4,068,657 A | | 1/1978 | Kobzan |
| 4,169,473 A | | 10/1979 | Samelson |
| 4,170,230 A | | 10/1979 | Nelson |
| 4,222,378 A | * | 9/1980 | Mahoney ............... 128/206.24 |
| 4,230,106 A | * | 10/1980 | Geeslin et al. ......... 128/201.11 |
| 4,233,972 A | | 11/1980 | Hauff et al. |
| 4,270,531 A | | 6/1981 | Blachly et al. |
| 4,304,227 A | | 12/1981 | Samelson |
| D263,166 S | * | 2/1982 | Bushman ..................... D24/17 |
| 4,331,141 A | | 5/1982 | Pokhis |
| 4,360,017 A | * | 11/1982 | Barlett ................. 128/202.28 |
| 4,495,945 A | | 1/1985 | Liegner |
| D295,797 S | * | 5/1988 | Bono et al. ..................... D29/6 |
| 4,862,903 A | | 9/1989 | Campbell |
| 4,881,540 A | * | 11/1989 | Vigilia .................. 128/202.28 |
| 5,031,611 A | * | 7/1991 | Moles ................... 128/201.11 |
| 5,062,422 A | * | 11/1991 | Kinkade ............... 128/207.14 |
| 5,117,816 A | | 6/1992 | Shapiro et al. |
| 5,174,284 A | * | 12/1992 | Jackson ................ 128/200.26 |
| 5,195,513 A | | 3/1993 | Sinko et al. |
| 5,203,324 A | | 4/1993 | Kinkade |
| 5,253,658 A | * | 10/1993 | King .......................... 128/859 |
| 5,265,591 A | | 11/1993 | Ferguson |
| 5,284,134 A | | 2/1994 | Vaughn et al. |
| 5,333,608 A | | 8/1994 | Cummins |
| 5,353,810 A | | 10/1994 | Kittelsen et al. |
| 5,389,024 A | * | 2/1995 | Chen .................... 128/202.15 |
| 5,438,978 A | * | 8/1995 | Hardester, III ......... 128/201.13 |
| 5,471,976 A | | 12/1995 | Smith |
| 5,492,114 A | | 2/1996 | Vroman |
| 5,513,634 A | * | 5/1996 | Jackson ................ 128/207.18 |
| 5,533,523 A | * | 7/1996 | Bass, Jr. et al. ............ 128/859 |
| 5,560,354 A | | 10/1996 | Berthon-Jones et al. |
| 5,570,702 A | * | 11/1996 | Forman ..................... 128/842 |
| 5,579,284 A | | 11/1996 | May |
| 5,590,643 A | | 1/1997 | Flam |
| 5,620,011 A | * | 4/1997 | Flowers ...................... 128/859 |
| 5,624,257 A | * | 4/1997 | Farrell ........................... 433/6 |
| 5,626,128 A | | 5/1997 | Bradley et al. |
| 5,638,811 A | | 6/1997 | David |
| 5,666,974 A | | 9/1997 | Hiro et al. |
| 5,682,878 A | | 11/1997 | Ogden |
| 5,682,904 A | * | 11/1997 | Stinnett ...................... 128/861 |
| 5,706,251 A | | 1/1998 | May |
| 5,720,656 A | | 2/1998 | Savage |
| 5,752,510 A | | 5/1998 | Goldstein |
| 5,792,067 A | * | 8/1998 | Karell ......................... 600/534 |
| 5,797,627 A | | 8/1998 | Salter et al. |
| 5,814,074 A | | 9/1998 | Branam |
| D399,950 S | * | 10/1998 | Shepard .................. D24/110.5 |
| 5,865,170 A | * | 2/1999 | Moles ................... 128/201.26 |
| 5,868,130 A | | 2/1999 | Stier |
| 5,884,625 A | | 3/1999 | Hart |
| 5,906,199 A | | 5/1999 | Budzinski |
| 5,921,241 A | * | 7/1999 | Belfer ......................... 128/848 |
| 5,947,116 A | | 9/1999 | Gamow et al. |
| 5,950,624 A | | 9/1999 | Hart |
| 5,957,133 A | | 9/1999 | Hart |
| 6,012,455 A | | 1/2000 | Goldstein |
| 6,073,626 A | | 6/2000 | Riffe |
| 6,076,526 A | * | 6/2000 | Abdelmessih ............... 128/848 |
| 6,079,410 A | | 6/2000 | Winefordner et al. |
| 6,089,225 A | * | 7/2000 | Brown et al. .......... 128/200.29 |
| 6,123,071 A | | 9/2000 | Berthon-Jones et al. |
| 6,148,818 A | | 11/2000 | Pagan |
| 6,192,886 B1 | | 2/2001 | Rudolph |
| 6,244,865 B1 | * | 6/2001 | Nelson et al. ............... 433/140 |
| 6,257,238 B1 | * | 7/2001 | Meah ......................... 128/859 |
| 6,263,877 B1 | * | 7/2001 | Gall ........................... 128/848 |
| 6,405,729 B1 | * | 6/2002 | Thornton ................... 128/848 |
| 6,427,696 B1 | * | 8/2002 | Stockhausen ............... 128/848 |
| 6,446,628 B1 | | 9/2002 | Chen |
| 6,494,209 B2 | * | 12/2002 | Kulick ....................... 128/848 |
| 6,514,176 B1 | * | 2/2003 | Norton ......................... 482/11 |
| 6,536,424 B2 | * | 3/2003 | Fitton .................... 128/200.24 |
| 6,536,428 B1 | | 3/2003 | Smith et al. |

FOREIGN PATENT DOCUMENTS

| | | | |
|---|---|---|---|
| WO | WO 9003199 | | 4/1990 |
| WO | WO 90/03199 | * | 4/1990 |
| WO | WO 9100075 | | 1/1991 |
| WO | WO 9603173 | | 2/1996 |

OTHER PUBLICATIONS

Journal of the Dental association of South Africa, Clinical trial of an oral vestibular shied for the control of snoring, Jan. 1993, pp. 15 16, and 17.
One sheet of pictures of prior art Mouthpiece.
One sheet of pictures of prior art Mouthpiece.
One sheet of pictures of prior art Mouthpiece.
One sheet of pictures of prior art Mouthpiece.

* cited by examiner

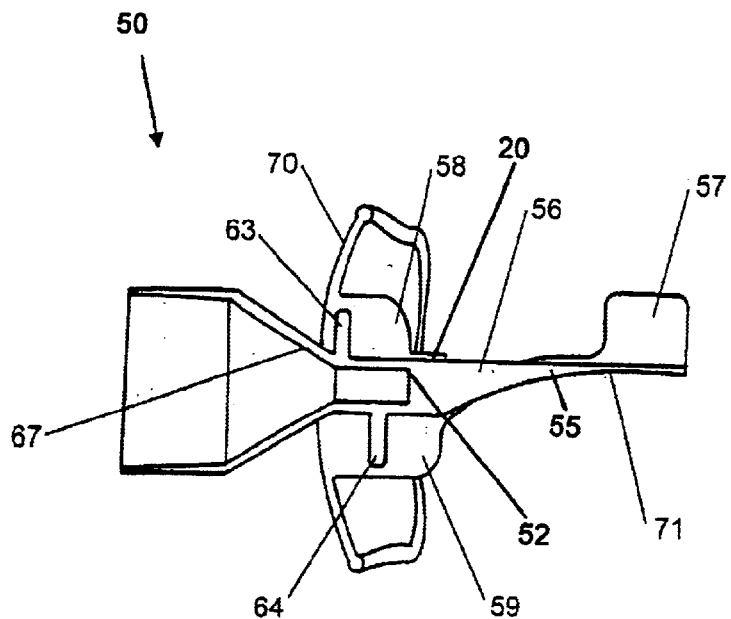
FIG. 4
FIG. 5
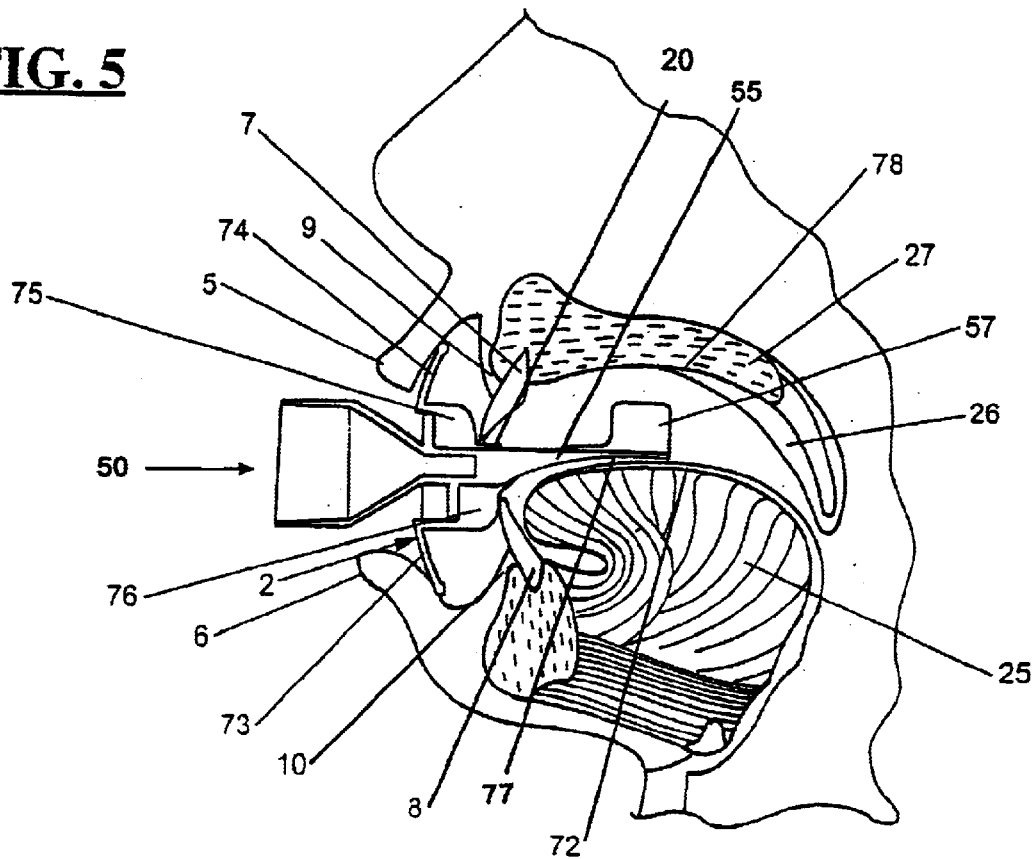

BREATHING ASSISTANCE APPARATUS

This application is a continuation-in-part application of U.S. patent application Ser. No. 09/326,478, filled on Jun. 4, 1999 and entitled "System, including a mouthpiece, for delivering pressurized gases to a user, abandoned Jul. 11, 2001.

BACKGROUND OF THE INVENTION

1. Field of Invention

This invention relates to a system for oral delivery of gases pressurized above ambient, and in particular, to a system, including a novel mouthpiece, for the oral delivery of air in continuous positive airway pressure (CPAP) treatments of sleeping disorders such as sleep apnoea.

2. Description of the Prior Art

Sleep apnoea treatments have been significantly advanced with the introduction of continuous positive airway pressure (CPAP) treatments. These treatments, as introduced, involve the supply of gases from a gases supply or blower to a patient through a conduit and nasal mask to provide an elevated internal pressure in the users airways to assist the muscles to keep the airways open. This airstream is provided to the user through a nasal mask applied over the nose and held in place by a harness. This configuration has been almost universally adopted based on the well known observation that humans show a decided preference for nasal breathing during sleep. For this reason, little development has been undertaken into other possible methods of providing the pressurized airstream to a user.

Oral delivery is suggested in EP 818,213, which shows an apparatus for oral delivery of air in a CPAP treatment. The apparatus includes a mouthpiece adapted to fit inside the mouth between the roof of the mouth, the hard palate, and the tongue, and having a periphery which can be gripped between the teeth. It is thought by the applicants that this is significantly more intrusive than is necessary and is liable to movement and consequent discomfort (although not outright removal) under the relaxation of sleep. It has the additional disadvantage that with the user fully relaxed, such as in the case of sleep, a distension in the user's jaw and subsequent opening of the mouth can reduce the sealing effectiveness of the mouthpiece and reduce the efficacy of the CPAP treatment.

Because the mouthpiece in EP 818,213 is gripped between the user's teeth, a further disadvantage results in that the mouthpiece requires custom orthodontic fitting to ensure that the mouthpiece matches the user's mouth and teeth layout. Custom orthodontic fitting is time consuming and removes the capability of effective mass manufacture. Consequently, the mouthpiece in EP 818,213 is expensive, creating a significant barrier to the patient adoption of the device.

A similar gases delivery mouthpiece, for use with a respirator, is shown in WO 90/03199. WO 90/03199 discloses an orthodontic device which is adapted to be gripped between the jaws of a user and to accommodate the user's teeth within a series of upper and lower cavities. A base member of the mouthpiece is shaped and fits against the hard palate of the user. This mouthpiece again has the disadvantage of requiring custom orthodontic fitting. Furthermore, as a result of the mouthpiece's substantial thickness and size, the mouthpiece is substantially rigid in the vestibule regions of the mouth. The mouthpiece is clamped in place by an outer shield which engages the outside of the user's lips.

A paper by E Veres entitled "Clinical trial of an oral vestibular shield for the control of snoring" (Journal of the Dental Association of South Africa, January 1993) describes the use of a shield intended to be retained in the vestibule of the mouth to seal the mouth and to promote nasal breathing which has been conventionally considered to be more beneficial than oral breathing. Humidified CPAP treatments delivered orally, however, actually derive greater benefit than those delivered nasally because secondary leakage through the nasal passages during oral delivery is significantly less than oral leakage during nasal delivery. The shield depicted in the paper is formed from flexible ethylene vinyl. The shield is custom trimmed and is custom fitted by heating to a malleable temperature and deformed by applied pressure.

Other possible mouthpiece designs are shown for example by use in self contained underwater breathing apparatus systems, for example as depicted in U.S. Pat. No. 4,862,909. This mouthpiece is a mouth guard type and is clamped between the teeth. A flange extends both in front of and behind the teeth.

Prior art mouthpieces are not well adapted for use in CPAP treatments because they are intended for conscious gripping by the user, and have been found subject to accidental removal with a user in a completely relaxed state such as sleep. The present invention overcomes this problem and present several other advantages which will become apparent upon a reading of the attached specification, in combination with a study of the drawings.

SUMMARY OF THE INVENTION

It is an object of the present invention to provide a system for oral delivery of gases, and/or a mouthpiece for oral delivery of gases, which goes some way toward overcoming the above disadvantages or which will at least provide the public with a useful choice.

Accordingly in a first aspect the present invention consists in a system capable of being used for oral delivery of gases pressurized above ambient to a user comprising: a mouthpiece; a breathing tube; and decoupling means for connecting said mouthpiece to said breathing tube, said decoupling means comprising a connection tube being formed of a material which is more flexible than the material of which said breathing tube is formed.

In a second aspect the present invention consists in a mouthpiece comprising: a generally rectangularly-shaped vestibular shield having an inner surface and an outer surface, said vestibular shield having a predetermined height which will overlap a user's teeth and gums when positioned in the mouth vestibule of a user, said vestibular shield having a central portion which will extend over a user's front teeth and gums when said central portion of said vestibular shield is positioned between the lips and the teeth of the user, and outer portions extending from said central portion which extend along and overlap at least a portion of the user's back teeth and gums when said outer portions of said vestibular shield are positioned between the cheeks and the teeth of the user; and gases passageway means extending from said outer surface of said vestibular shield to said inner surface of said vestibular shield for allowing the passage of said gases through said mouthpiece.

In a third aspect the present invention consists in a mouthpiece comprising:

a vestibular shield having an inner surface and an outer surface, said vestibular shield having a predetermined height which will overlap a user's teeth and gums when positioned in the mouth vestibule of a user;

gases passageway means extending from said outer surface of said vestibular shield to said inner surface of said vestibular shield for allowing the passage of said gases through said mouthpiece; and extra-oral sealing means associated with said gases passageway which may be adjusted into one of two configurations, a first condition when said mouthpiece is inserted into a user's mouth being substantially unengaged with a user's face, and a second condition when correctly positioned in a user's mouth being substantially engaged with a user's face and under compression thereupon.

In a fourth aspect in a first aspect the present invention consists in a system capable of being used for oral delivery of gases pressurized above ambient to a user comprising:

gases supply means, a gases passageway in fluid communication with said gases supply means, and a mouthpiece in fluid communication with said gases passageway including an intra-oral sealing means and an extra-oral sealing means.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

The invention consists in the foregoing and also envisages constructions of which the following gives examples.

BRIEF DESCRIPTION OF THE DRAWINGS

One preferred form of the present invention will now be described with reference to the accompanying drawings in which;

FIG. 4 is a cross-section of the mouthpiece of FIG. 2, FIG. 5 is a cross-sectional view of the mouthpiece of FIG. 2 and a user with the mouthpiece in place to demonstrate the location and positioning thereof in relation to the main features of the user's anatomy.

DETAILED DESCRIPTION OF THE PREFERRED EMBODIMENTS

Figure 1:
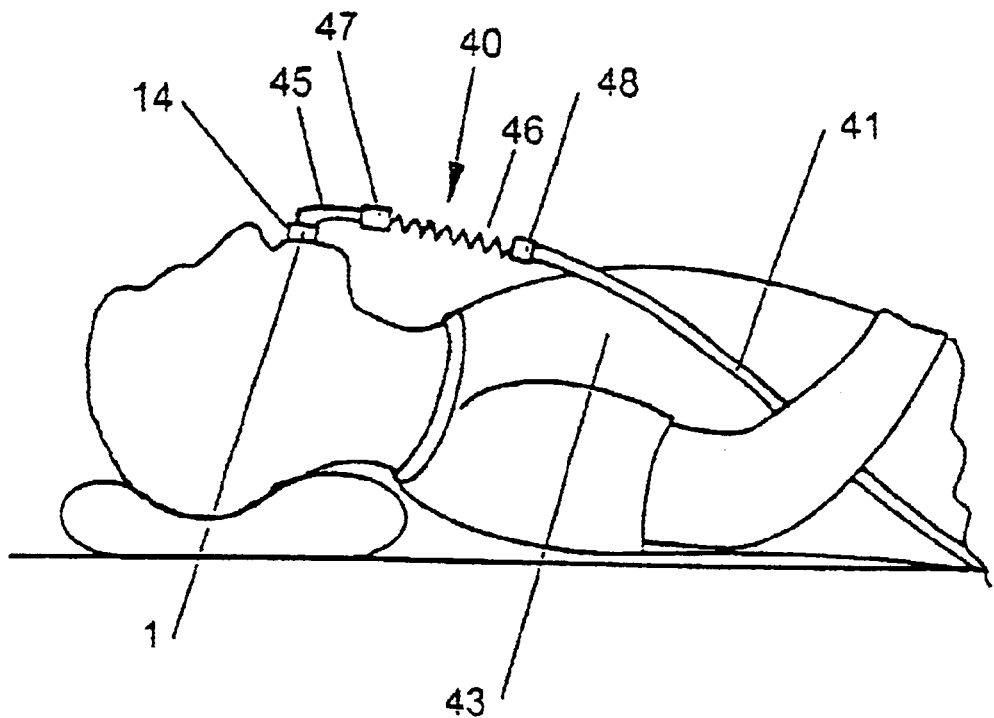
FIG. 1 is a side elevational view of the system according to the present invention as being used by a patient.

While the invention may be susceptible to embodiment in different forms, there is shown in the drawings, and herein will be described in detail, specific embodiments with the understanding that the present disclosure is to be considered an exemplification of the principles of the invention, and is not intended to limit the invention to that as illustrated and described herein.

The present invention provides a novel system for oral delivery of gases pressurised above ambient to a user and is especially suited for use in the oral delivery of air in continuous positive airway pressure (CPAP) treatments of sleeping disorders such as sleep apnea. As shown in FIG. 1, the system includes a mouthpiece 1 which is connected by a connection 40 to a breathing circuit 41.

A preferred embodiment of the present invention is illustrated in FIGS. 2 to 5. In this embodiment, the mouthpiece 50 includes a vestibular shield 2 being a generally flat and generally rectangularly-shaped member in front elevation having a curved profile that reflects the curvature of a user's jaw and in turn the curvature of the labial vestibule region (the regions between the lips 5, 6 and the front teeth 7, 8 and the front gums 9, 10, as shown in FIG. 5). The vestibular shield has an inner surface 3 and outer surface 13. A gases passageway extends through the vestibular shield from an inlet 51 to an outlet 52 through the central portion 14 of the vestibular shield 2. The vestibular shield is dimensioned such that outer portions 4 extend from the central portion 14 and around the sides of the labial vestibule into the buccal vestibule region (the region between the back teeth and the cheeks). As shown in FIG. 5, the vestibular shield 2 has a vertical dimension or predetermined height such that the upper and lower edges 73, 74 of the shield 2 extend beyond the margins of the users teeth 7, 8 to overlap the gums 9, 10 in the labial vestibule region. This vertical dimension is generally consistent along the horizontal length of the vestibular shield 2, such that the upper and lower edges 73, 74 of the vestibular shield 2 extend beyond the margins of the back teeth in the buccal vestibule region to overlap the gums of the back teeth. In the preferred embodiment the inlet 51 is provided by a flattened oval-shaped connector 53. The outlet 52 has an even more laterally extended flattened oval shape 54. The major differences between the mouthpiece 50 and the embodiments described above are provided on the inner surface 3 of the vestibular shield. Most prominently, the mouthpiece 50 includes a tongue depressor 55 extending from the inner face of the vestibular shield 2. The operation of the tongue depressor will be described further on with reference to FIG. 5. The tongue depressor includes a vertical stiffening flange 56 centrally located on its upper surface and extending from the gases outlet 52. In use gases flow easily around the stiffening flange 56 effectively bifurcating the gases outlet 52. The tongue depressor 55 further includes a pair of vertically extending spacers 57 which in use may abut against the roof of the wearer's mouth and ensure that the tongue cannot completely block the air passageway. In the mouthpiece 50 the sealing effect of the vestibular shield 2 against the lips of the user is enhanced by providing teeth abutments of significantly increased thickness than the raised area 20 of the earlier embodiments. In particular, an upper teeth abutment 58 and a lower teeth abutment 59 are provided, with the lower teeth abutment 59 protruding further from the inner face of the vestibular shield 2 than the upper teeth abutment 58. This difference serves to match the typical over-bite of most users. The abutments 58 and 59 are not required to be wider than the gases outlet 52.

A notch 60 is provided centrally in the upper edge of the vestibular shield 2 to accommodate the upper frenal attachment. A slight bead 61 is provided around the edge of the vestibular shield 2 for user comfort, with the vestibular shield 2 otherwise being very thin for additional suppleness.

Referring particularly to FIG. 4, in its preferred form the mouthpiece 50 is preferably formed by over-moulding a soft and supple material part 70 over a stiffer material part 67. These can generally be termed the shield part and the passageway-forming insert. The passageway-forming insert preferably includes a pair of upper and lower vertical flanges 63 and 64 to fully engage within the supple material. The passageway-forming insert 67 includes the vertically extending stiffening flange 56 of the tongue depressor 55, together with a curved planar portion 71 forming the backbone of the tongue depressor 55. The vertically extending spacers 57 are of the soft and supple material and are part of the over-moulding 70, as are the upper and lower teeth abutments 58 and 59.

Figure 2:
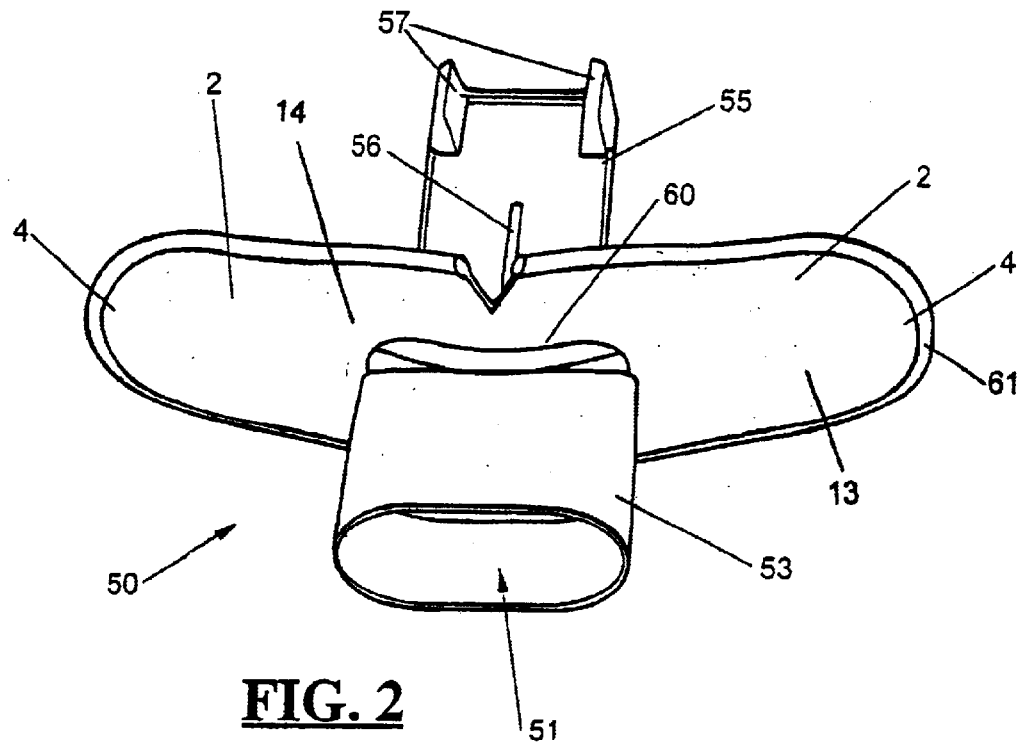
FIG. 2 is a perspective view from above of a mouthpiece according to the preferred embodiment of the present invention.
Figure 3:
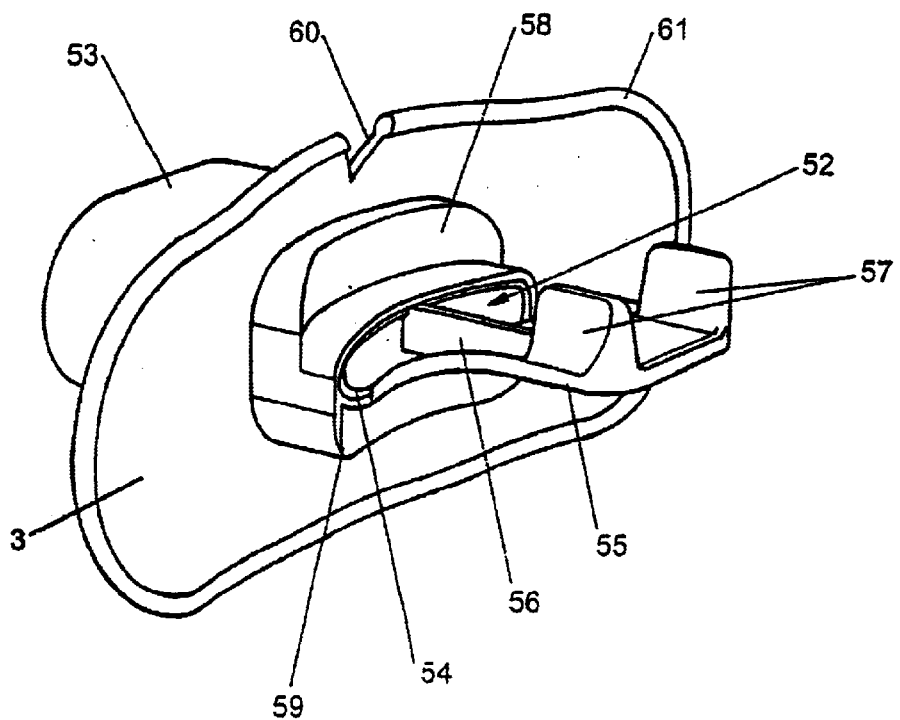
FIG. 3 is a perspective view from one side and from an inward direction of the mouthpiece of FIG. 2.

Referring now to FIG. 5, use of the mouthpiece according to FIGS. 2 to 4 is depicted. With the present mouthpiece 50, the upper and lower lips 5, 6 are further distended by the abutment action of the abutments 75, 76 against the upper and lower teeth 7, 8 respectively, thus forming a seal of greater pressure between the lips 5, 6 and the upper and lower portions respectively of the vestibular shield 2. A lower face 77 of the tongue depressor 55 impinges if necessary on the upper surface 72 of the tongue 25 and retains the tongue in the lower portion of the mouth. This ensures a clear gases outlet 52 from the gases passageway through the vestibular shield. The vertically extending spacers 57, if forced by pressure from the tongue, will engage against the roof of the user's mouth and maintain a clear air passageway. This stops the sleeping patient unconsciously blocking the oral passageway and reverting to nasal breathing.

Attention is now directed to FIG. 1. It has been found that an additional factor in the effectiveness of any mouthpiece, including mouthpiece 1, is the manner in which the mouthpiece is connected to the breathing circuit 41. The weight of the breathing circuit 41, and any attempted movement of one other of the breathing circuit 41 and the mouthpiece 1 relative to the other, is one of the largest influences tending to dislodge a mouthpiece 1 from the mouth of a user. It must be noted that the mouthpiece 1 must remain in position and maintain a seal during all sleep, when the user has no muscle tone.

The connection 40 as provided in the present invention between the breathing circuit 41 and the mouthpiece 1 decouples the mouthpiece 1 from the breathing circuit 41. As a result, the connection 40 is effective in reducing the forces placed on the mouthpiece 1 by the breathing circuit 41 when the user moves around during sleep. In the preferred sleeping position, the breathing circuit 41 is laid across the chest 43 of the user, and may be secured to the user's bed clothes or sleeping garments. The breathing circuit 41 is preferably laid on the chest of the user to take the weight of the breathing circuit 41 off of the mouthpiece 1.

To connect between the gases outlet 14 which is vertical when the user is laying on his or her back and the breathing circuit 41 which is generally horizontal, an L-shaped elbow 45 is incorporated in the connection 40. The elbow 45 may be incorporated in the mouthpiece 1, however, it is preferred that the mouthpiece 1 be kept small to provide for easier cleaning. The elbow 45 is formed at a right angle and provides a positive pressure on the mouthpiece 1 to maintain the mouthpiece 1 in the user's mouth. The elbow 45 may include a swivel joint and may be disconnected from gaseous outlet 14. The connection 40 further includes an extremely flexible connecting tube 46 provided between the elbow 45 and the breathing circuit 41. The connecting tube 46 is preferably connected to the breathing circuit 41 by a swivel joint 48 for reasons described herein. The breathing circuit 41, while flexible, will necessarily be stiff enough to maintain its integrity over comparatively long turns, while the connecting tube 46, being only a short length, for example 10 centimetres, merely has to span between the user's mouth and chest, and can thereby be made in a manner that would not be suitable for long runs. Furthermore, as a result of the short length of the connecting tube 46, the connecting tube 46 does not need to incorporate significant insulation or heating capability. The connecting tube 46 may be formed from a thin plastic membrane supported over a helical or double helical or corrugated supporting ribs. In such a case, the support makes the connection tube 46 laterally flexible and resistant to torsion. The elbow swivel joint 45 allows for movement of the connection tube 46 relative to the mouthpiece 1. The swivel joint 48 allows for movement of the connection tube 46 relative to the breathing circuit 41. It is to be understood that one or both of the swivel joints 45, 48 could be eliminated, but the preferred embodiment includes swivel joint 48.

Figure 6:
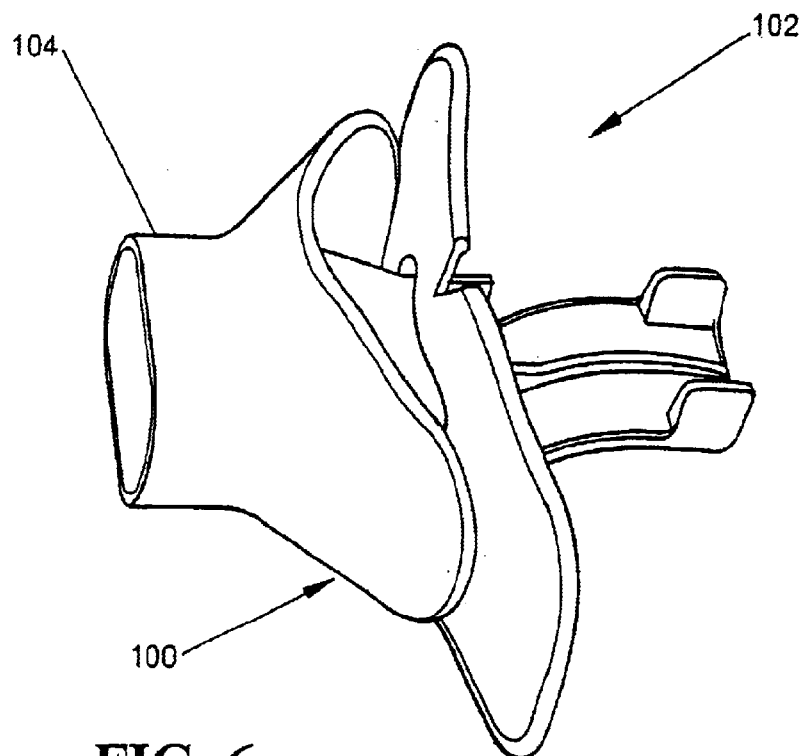
FIG. 6 is a perspective view of the mouthpiece with the outer flap in place.

Referring now to FIG. 6 of the present invention is illustrated including an extra-oral sealing means 100. The extra-oral sealing means is preferably a flap 100 which in its natural bias is tapered, the wide open end of which is shaped to conform to the facial contours around the outside of the mouth of a user. The narrow end joins to a cylindrical section, which is designed to slide over the inlet port 104 of the mouthpiece 102. Therefore, the flap 100 is detachable from the gases passageway. While this is one method of attachment the flap 100 might also be constructed as an integral part of the mouthpiece 102. The flap 100 needs to be constructed of flexible material, therefore materials such as silicone rubber can be employed to fashion the flap.

Figure 7:
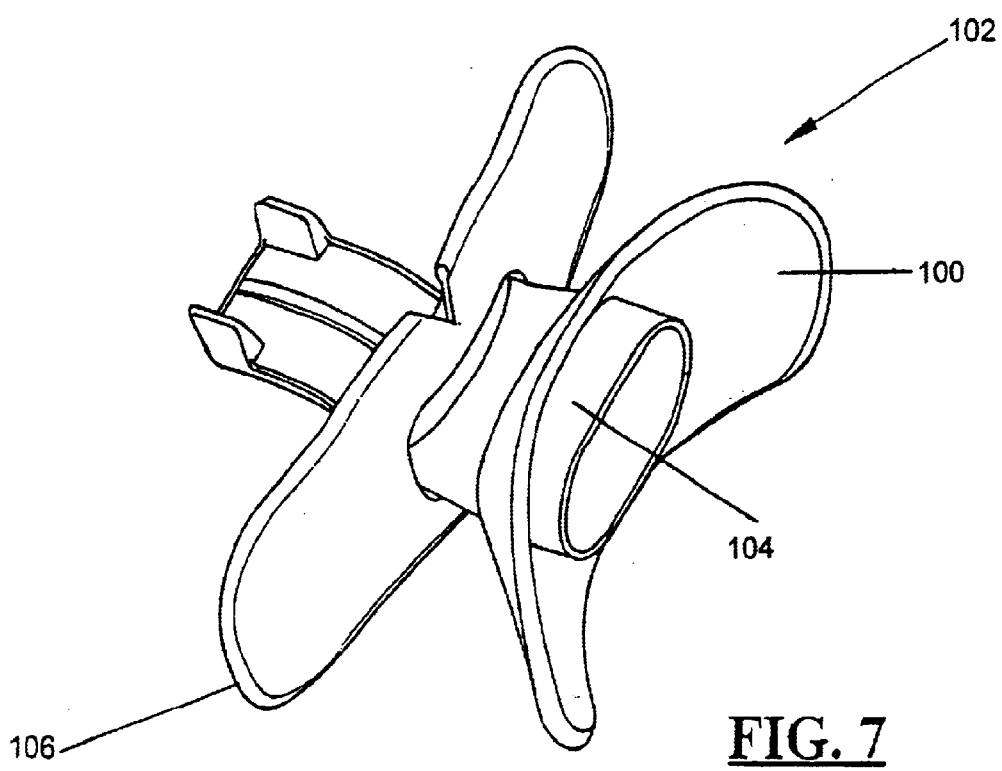
FIG. 7 is a perspective view of the outer flap bent back.

The outer flap 100 is seen in FIG. 7, in a bent back position. It will be appreciated that when the mouthpiece 102 is being inserted into the mouth of a user, the outer flap 100 is intended to be in this bent back position to aid insertion. Prior to insertion, the outer flap is bent back by simply pressing on its outer periphery 106, until it snaps into the bent back position, in which it will stay unaided.

Figure 8:
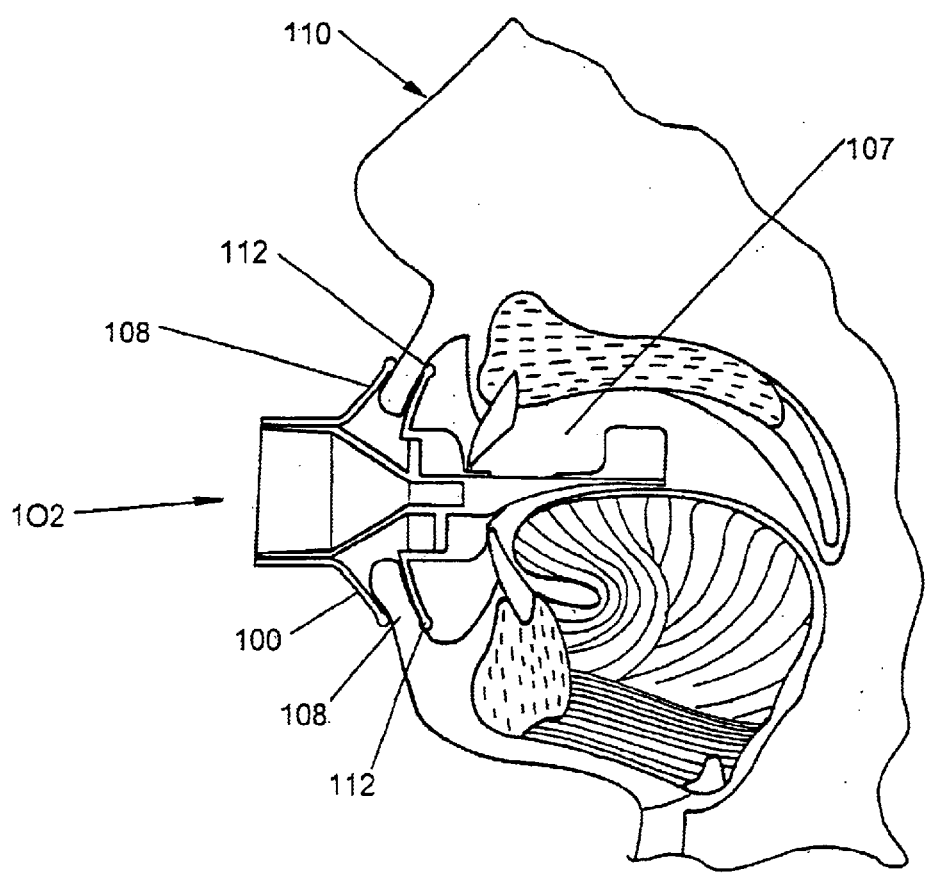
FIG. 8 is a cutaway view of the present invention with the outer flap in use.

In FIG. 8 we see the outer flap 100 in use with the mouthpiece 102 in the mouth 107 of a user 110. Once correctly positioned in the mouth 106, the outer flap 100 may be adjusted into its operational position by pressing on its outer periphery 106 until it snaps back to press against the outside of the mouth 108. Due to the relative position of the vestibular shield 112 and the outer flap 100, the outer flap 100 is unable to fully reach its natural bias and thereby inflicts a compressive force on the outside of the mouth 108.

It will be appreciated that as well as providing a substantially airtight seal the addition of the outer flap provides enough compressive force on the mouth to keep the mouthpiece and conduit in place without the need for straps. This allows the administering of CPAP therapy to be considerably less obtrusive than traditional methods.

Figure 9:
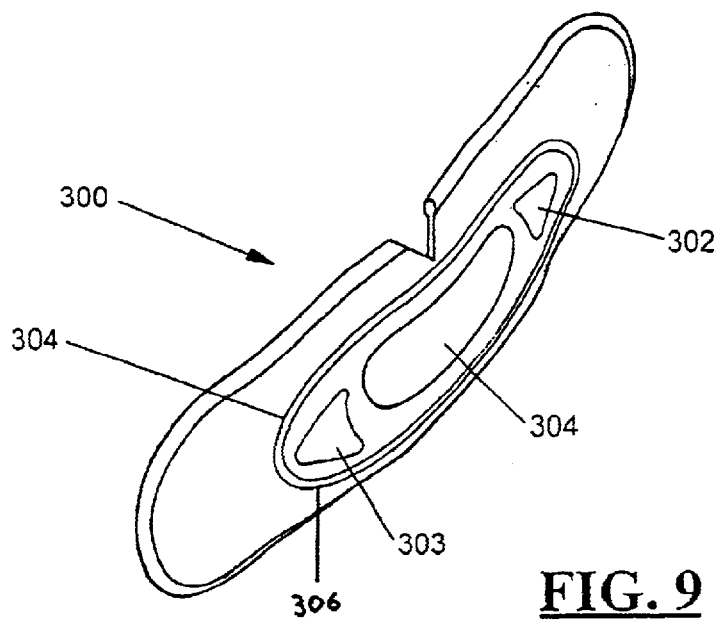
FIG. 9 is a perspective view of the outer flap including the ventilation apertures and moisture barrier.

In a further additional improvement shown in FIG. 9, the outer flap 300 is shown in perspective. Included are ventilation apertures 302, 303 either side of the gases port 304, which are surrounded by a ridge 306 acting as a moisture barrier. The apertures 302, 303 are provided such that any excess moisture leaking from the mouth will migrate to the apertures where they may evaporate. Small vents in the conduit may be used to direct small amounts of pressurised gas at the apertures to aid evaporation. The ridge 306 is included to ensure that no moisture migrates further into the sealing region 308, as this would be detrimental to the sealing properties of the flap.

Figure 10:
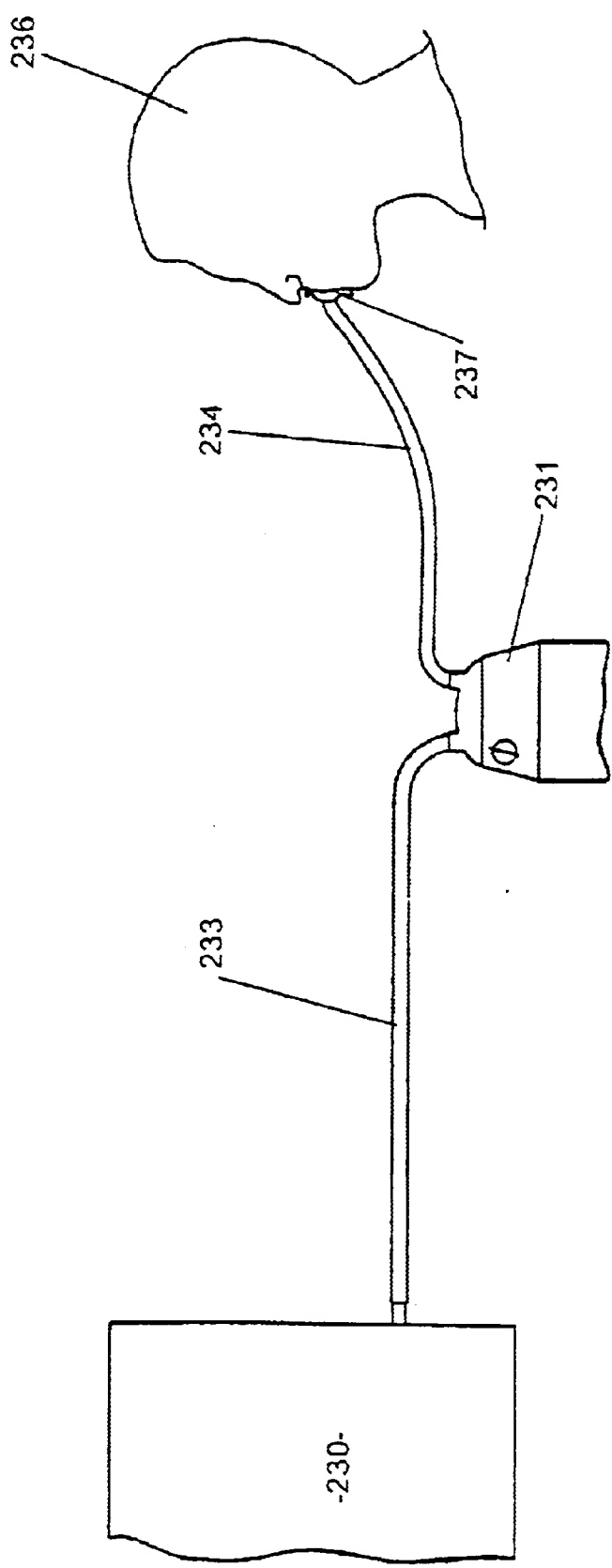
FIG. 10 is a block diagram of a respiratory system according to the preferred embodiment of the present invention.

A typical respiratory humidification circuit such as might employ the present invention is shown diagrammatically in FIG. 10, and includes the respirator 230, humidifier 231, and the associated respiratory breathing tubes 233 and 234. A patient 236 under treatment is shown, with the present invention 237, located in the mouth of the patient 236.

From the above it can be seen that the present invention provides a system including mouthpiece 1 for oral delivery of CPAP treatment which at once is low cost and effective. Unlike other appliances the mouthpiece 1 used in the present invention does not require custom orthodontic fitting as the mouthpiece 1 does not rely on accurate alignment with the user's teeth or the user's palate to provide location and retention within the user's mouth, but instead resides in the vestibule between the teeth and lips and the teeth and cheeks, and the lateral and vertical extension of the vestibular shield 2 requires that the user's lips be actively manipulated for the vestibular shield 2 to be removed. Furthermore the improved connection 40 to the breathing circuit 41 reduces the forces which tend to pull at the mouthpiece 1. With the addition of the extra-oral flap 100, the mouthpiece and associated tubing is held securely in place without the need for external strapping, and an effective seal is created around the users mouth.

What is claimed is:

1. A mouthpiece for delivering positive pressure gases to the oral cavity of a user comprising: a generally rectangularly-shaped vestibular shield having an inner surface and an outer surface, said vestibular shield having a predetermined height which will overlap a user's upper and lower teeth and gums when positioned in the mouth vestibule of a user, said vestibular shield having a central portion which will extend over a user's front teeth and gums when said central portion of said vestibular shield is positioned between the lips and the teeth of the user, and outer portions extending from said central portion which extend along and overlap at least a portion of the user's back teeth and gums when said outer portions of said vestibular shield are positioned between the cheeks and the teeth of the user, said vestibular shield in use sealing against the inner walls of the lips and/or cheeks of a user's mouth; and gases passageway means extending from said outer surface of said vestibular shield to said inner surface of said vestibular shield to allow said gases to flow through said mouthpiece; and a gases outlet adapted to expel said gases from said gases passageway means into the oral cavity of a user.

2. A mouthpiece as claimed in claim 1 wherein said mouthpiece further includes a raised portion provided on said inner surface of said central portion of said vestibular shield, said raised portion solely contacting the teeth of a user when said vestibular shield is placed in the mouth of a user.

3. A mouthpiece as claimed in claim 2 wherein said raised portion is of a generally flattened oval shape.

4. A mouthpiece as claimed in claim 3 wherein said raised portion extends along at least a portion of said outer portions.

5. A mouthpiece as claimed in claim 2 wherein said raised portion includes an upper abutment portion for abutting against the user's upper teeth and a lower abutment portion for abutting against the user's lower teeth and the lower abutment portion extends further out from the inner surface of the vestibular shield than said upper abutment portion.

6. A mouthpiece as claimed in claim 1 wherein said central portion includes a centrally located notch in a top edge thereof.

7. A mouthpiece as claimed in claim 1 wherein said vestibular shield has a generally curved profile.

8. A mouthpiece as claimed in claim 1 wherein said gases passageway means includes gases inlet means for allowing connecting of said mouthpiece to a gases supply.

9. A mouthpiece as claimed in claim 1 wherein said gases inlet means is connected to said central portion of said vestibular shield.

10. A mouthpiece as claimed in claim 1 wherein said vestibular shield is formed of a supple material and said gases inlet means comprises a tube formed of a stiffer material than said supple material that is used to form said vestibular shield, said tube being attached to said vestibular shield.

11. A mouthpiece as claimed in claim 1 wherein said gases outlet means is provided along said central portion of said vestibular shield.

12. A mouthpiece as claimed in claim 11 wherein said gases passageway means includes gases inlet means for allowing connection of said mouthpiece to a gases supply.

13. A mouthpiece as claimed in claim 12 wherein said gases outlet means is aligned with said gases inlet means.

14. A mouthpiece as claimed in claim 13 wherein said gases inlet means and said gases outlet means are connected to said central portion of said vestibular shield.

15. A mouthpiece as claimed in claim 14 wherein said gases outlet means is a generally flattened oval-shaped tube which extends from said gases inlet means, through said inner surface of said vestibular shield and out from said inner surface.

16. A mouthpiece as claimed in claim 15 wherein said vestibular shield is formed of a supple material.

17. A mouthpiece as claimed in claim 16 wherein said vestibular shield is generally flat.

18. A mouthpiece as claimed in claim 17 wherein each said outer portion has rounded upper and lower edges.

19. A mouthpiece as claimed in claim 1 including a tongue depressing guard extending from the inner surface of said vestibular shield, said tongue depressing guard having an upper surface and lower surface.

20. A mouthpiece as claimed in claim 19 wherein said tongue depressing guard has a concave curve in its lower surface and is stiffer than the outer portions of said vestibular shield.

21. A mouthpiece as claimed in claim 20 wherein said mouthpiece including one or more vertically extending spacers projecting from the upper surface of said tongue depressing guard.

22. A mouthpiece as claimed in claim 21 wherein said gases passageway means is provided by an insert of substantially stiffer material than the material of said vestibular shield, said insert extending through said vestibular shield, where said tongue depressing guard is an extension of said insert into said user's mouth when in use.

23. A mouthpiece as claimed in claim 10 wherein said mouthpiece includes extra-oral sealing means.

24. A mouthpiece as claimed in claim 1 wherein said extra-oral sealing means may be adjusted into one of two configurations, a first configuration when said mouthpiece is inserted into said user's mouth with said extra-oral sealing means substantially unengaged with said user's face, and a second configuration when said mouthpiece is positioned in said user's mouth said extra-oral sealing means is substantially engaged with and compressed against said user's face.

25. A mouthpiece comprising:

a vestibular shield having an inner surface and an outer surface, said vestibular shield having a predetermined height which will overlap a user's teeth and gums when positioned in the mouth vestibule of a user;

gases passageway means extending from said outer surface of said vestibular shield to said inner surface of said vestibular shield for allowing for the passage of gases through said mouthpiece; and extra-oral sealing means associated with said gases passageway means which may be adjusted into one of two configurations, a first configuration when said mouthpiece is inserted into a user's mouth with said extra-oral sealing means substantially unengaged with a user's face, and a second configuration when said mouthpiece is positioned in a user's mouth with said extra-oral sealing means substantially engaged with and compressed against a user's face.

26. A mouthpiece as claimed in claim 25 wherein said extra-oral sealing means are detachable from said gases passageway means.

27. A mouthpiece as claimed in claim 25 wherein said extra-oral sealing means are constructed of silicon rubber.

28. A mouthpiece as claimed in claim 25 wherein said extra-oral sealing means comprise at least one tapered flap.

29. A mouthpiece as claimed in claim 28 wherein said at least one tapered flap has a wide end and a narrow end, said narrow end being attached to said gases passageway means.

30. A mouthpiece as claimed in claim 29 wherein said first configuration comprises said wide end being distant to the oral cavity of a user relative to said narrow end being proximate to the oral cavity of a user.

31. A mouthpiece as claimed in claim 29 wherein said second configuration comprises said wide end being proximate to the oral cavity of a user relative to said narrow end being distant to the oral cavity of a user.

32. A mouthpiece as claimed in claim 29 wherein said wide end is adapted to conform to the facial contours of a user.

33. A mouthpiece as claimed in claim 28 wherein said at least one tapered flap includes at least one ventilation means.

34. A mouthpiece as claimed in claim 33 wherein said narrow end and said at least one ventilation means are surrounded by a ridge on said flap which in use faces a user.

35. A mouthpiece as claimed in claim 33 wherein said at least one ventilator means comprises two apertures between of said narrow end and said wide end.

36. A mouthpiece as claimed in claim 35 wherein said mouthpiece includes means which are adapted to direct a small amount of pressurised gases toward said apertures.

37. A mouthpiece as claimed in claim 29 wherein when said extra-oral sealing means is in said second configuration a compressive force exists between said vestibular shield and said extra-oral sealing means on a user's face and said compressive force is sufficient to secure said mouthpiece in place on a user and to provide a substantial seal thereto.

* * * * *

UNITED STATES PATENT AND TRADEMARK OFFICE
CERTIFICATE OF CORRECTION

PATENT NO.    : 6,679,257 B1                                                Page 1 of 1
DATED         : January 20, 2003
INVENTOR(S)   : Christopher John Robertson, Nicholas Charles Alan Smith and Lewis George Gradon It is certified that error appears in the above-identified patent and that said Letters Patent is hereby corrected as shown below:

Title page,
Item [63], Related U.S. Application Data, "filed on June 4, 1998" should read
-- filed on June 4, 1999 --

Column 8,
Line 49, "as claimed in claim 10" should read -- as claimed in claim 1 --

Column 10,
Line 18, "as claimed in claim 29" should read -- as claimed in claim 25 --

Signed and Sealed this

Fourth Day of May, 2004

JON W. DUDAS
*Acting Director of the United States Patent and Trademark Office*